(12) United States Patent
Lipinski et al.

(10) Patent No.: US 10,517,807 B2
(45) Date of Patent: Dec. 31, 2019

(54) HAIR CLEANSING COMPOSITION WITH IMPROVED COLOR RETENTION ON PRE-COLORED KERATIN FIBERS AND IMPROVED FOAM PROPERTIES

(71) Applicant: KAO GERMANY GMBH, Darmstadt (DE)

(72) Inventors: Normen Lipinski, Darmstadt (DE); Huma Younas, Darmstadt (DE); Andreas Picker, Darmstadt (DE)

(73) Assignee: KAO Germany GmbH, Darmstadt (DE)

(*) Notice: Subject to any disclaimer, the term of this patent is extended or adjusted under 35 U.S.C. 154(b) by 78 days.

(21) Appl. No.: 15/787,950

(22) Filed: Oct. 19, 2017

(65) Prior Publication Data

US 2018/0104166 A1    Apr. 19, 2018

(30) Foreign Application Priority Data

Oct. 19, 2016  (EP) .................................... 16194495

(51) Int. Cl.
| | | |
|---|---|---|
| *A61Q 5/02* | (2006.01) | |
| *A61K 8/42* | (2006.01) | |
| *A61Q 5/12* | (2006.01) | |
| *A61Q 5/06* | (2006.01) | |
| *A61K 8/46* | (2006.01) | |
| *A61K 8/06* | (2006.01) | |
| *A61K 8/73* | (2006.01) | |
| *A61K 8/898* | (2006.01) | |
| *A61K 8/86* | (2006.01) | |
| *A61K 8/34* | (2006.01) | |

(52) U.S. Cl.
CPC ................ *A61K 8/42* (2013.01); *A61K 8/068* (2013.01); *A61K 8/345* (2013.01); *A61K 8/463* (2013.01); *A61K 8/466* (2013.01); *A61K 8/73* (2013.01); *A61K 8/86* (2013.01); *A61K 8/898* (2013.01); *A61Q 5/02* (2013.01); *A61Q 5/06* (2013.01); *A61Q 5/12* (2013.01); *A61K 2800/88* (2013.01)

(58) Field of Classification Search
None
See application file for complete search history.

(56) References Cited

FOREIGN PATENT DOCUMENTS

| EP | 2 039 751 A1 | 3/2009 |
|---|---|---|
| EP | 2 161 014 A1 | 3/2010 |
| EP | 2 161 017 A1 | 3/2010 |
| EP | 2 184 051 A1 | 5/2010 |
| EP | 2 586 421 A1 | 5/2013 |
| WO | 2013/098210 A1 | 7/2013 |

OTHER PUBLICATIONS

Matthews, Melissa; Woman's Day; "WD's Guide to At-Home Hair Dyeing Follow these seven easy steps for a salon-quality coloring job"; (https://www.womansday.com/style/beauty/a1711/wds-guide-to-at-home-hair-dyeing-108643/); published Jun. 29, 2010.*
European Search Report dated Dec. 21, 2016 corresponds to EP application No. 16194495.4.

* cited by examiner

*Primary Examiner* — Jeffrey T. Palenik
(74) *Attorney, Agent, or Firm* — Norris McLaughlin, P.A.

(57) ABSTRACT

The present invention is directed to a composition comprising a combination of surfactants for cleansing keratin fibers, a method for cleansing, use of the composition for cleansing, and kit-of-parts thereof. It has been found that the combination of two anionic surfactants, an amphoteric surfactant, and a diol compound provide a rich foam and superior color retention on pre-colored hair.

19 Claims, No Drawings

HAIR CLEANSING COMPOSITION WITH IMPROVED COLOR RETENTION ON PRE-COLORED KERATIN FIBERS AND IMPROVED FOAM PROPERTIES

This application claims foreign priority benefit of European Patent Application No. 16194495.4, filed Oct. 19, 2016, the disclosure of which patent application in its entirety is incorporated herein by reference.

The present invention relates to a hair cleansing composition with improved color retention for pre-colored keratin fibers. Moreover, a method of hair cleansing employing the composition is disclosed as well as a use of the composition, and kit-of-parts thereof.

Many cleansing compositions are known from literature which serve the main purpose of hair cleansing (WO99058106, WO2014053382, CN104095771, US2008095733). Besides cleansing, consumers with artificially colored hair desire to prevent the color in order to extend lifetime of the beautiful hair color. Currently marketed products already claim to provide a certain level of protection (Mintel #2800827, WO2012168061). However, consumers are still not fully satisfied with the performance of cleansing compositions and also desire rich foam and foam stability at the same time, which is typically achieved with high surfactant concentrations exceeding 20% by weight (EP0841898). But such high surfactant concentration is disadvantageous as they are less favourable in ecological profiles and cause in general higher color wash out. Moreover, there are disclosures on how to achieve rich and creamy foam by other means (WO2014053382). However, when foam properties are improved, this may be disadvantageous for the color of pre-colored hair as it may wash out faster. Thus, environment-conscious consumers are more and more aware of this issue while demanding environmentally friendly products without compromising product performances.

The present invention solves the aforementioned problems by employing an amount of surfactants below 19% by weight, calculated to the total of the composition, while enhancing foam volume, foam stability, and enhanced color retention on pre-colored hair. Thus, the present invention also reduces the environment footprint of cosmetic products.

The inventors of the present invention have surprisingly found that a cleansing composition comprising less than 19% by weight surfactant in total, wherein it further comprises a combination of at least two anionic surfactants, at least one amphoteric surfactant, and at least one diol compound solves the above addressed problems. Moreover, the literature is silent on the core of the present invention.

Thus, the first object of the present invention is an aqueous cleansing composition for keratin fibers, preferably for human hair, characterized in that it comprises surfactants at a total concentration in the range of 8% to 19% by weight, calculated to the total of the composition, wherein it comprises the following surfactants
a) a first anionic surfactant selected from compounds according to the structure

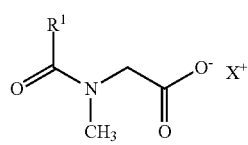

Formula I wherein $R^1$ is a straight or branched, substituted or unsubstituted, saturated or unsaturated alkyl chain with a carbon number of $C_9$ to $C_{21}$, preferably $R^1$ is a straight alkyl chain with a carbon number of $C_9$ to $C_{17}$, and $X^+$ is a cation selected from sodium, potassium, magnesium and ammonium ions,
b) a second anionic surfactant which is an alkyl sulfate or preferably ethoxylated alkyl ether sulfate surfactant or mixtures thereof with an alkyl chain length of $C_{10}$ to $C_{22}$,
c) an amphoteric surfactant selected from compounds according to the general structure(s) II and/or III

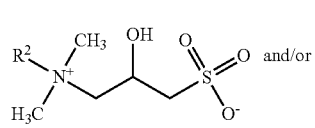

Formula II

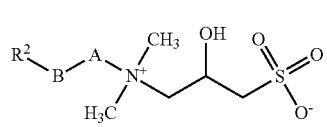

Formula III wherein $R^2$ is a straight or branched, saturated or unsaturated, substituted or unsubstituted alkyl chain with a carbon number of $C_{10}$ to $C_{22}$, preferably $R^2$ is a straight alkyl chain with a carbon number of $C_{10}$ to $C_{16}$, A is a straight alkyl chain with a carbon number of $C_1$ to $C_6$ or a branched alkyl chain with a carbon number of $C_3$ to $C_6$, preferably A is a linear alkyl chain with a carbon number of $C_3$, and B is an amide or an ester group.
d) a compound according to the general structure

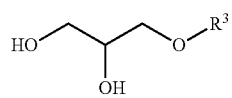

Formula IV wherein $R^3$ is a linear or branched alkyl chain with a carbon number of $C_3$ to $C_{12}$, preferably $C_3$ to $C_8$, more preferably $R^3$ is a branched alkyl chain with a carbon number of $C_8$.

The second object of the present invention is a method for cleansing artificially colored keratin fibers, preferably artificially colored human keratin fibers, more preferably artificially colored human hair, wherein the composition as defined above is applied onto wet hair, massaged and rinsed off with water after a treatment time in the range from 30 s to 600 s, preferably from 30 s to 300 s, more preferably from 30 s 10 to 100 s.

The third object of the present invention is the use of the composition as defined above for cleansing and reducing wash fastness of artificially colored keratin fibers, preferably artificially colored human keratin fibers, more preferably artificially colored human hair.

The fourth object of the present invention is a kit-of-parts comprising the composition as defined above and at least one further item selected from a hair conditioning composition and/or a hair styling composition.

The first anionic surfactant is selected from compounds according to the structure

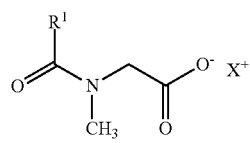

Formula I wherein $R^1$ is a straight or branched, substituted or unsubstituted, saturated or unsaturated alkyl chain with a carbon number of $C_9$ to $C_{21}$, preferably $R^1$ is a straight alkyl chain with a carbon number of $C_9$ to $C_{17}$, and $X^+$ is a cation selected from sodium, potassium, magnesium and ammonium ions, which are compounds based on the amino acid sarcosin which are commonly known as sarcosinates.

Suitable compounds are, for example, cocoyl sarcosinate and its salts, lauroyl sarcosinate and its salts, myristoyl sarcosinate and its salts, stearoyl sarcosinate and its salts, oleoyl sarcosinate and its salts, palmitoyl sarcosinate and its salts. Salts are formed with cations selected from sodium, potassium, magnesium, and ammonium ions.

The preferred surfactant of a) according to the structure of formula I is sodium lauroyl sarcosinate.

The total concentration of surfactant a) is in the range of 0.1% to 3.5% by weight, preferably 0.2% to 3.5% by weight, more preferably 0.5% to 3.5% by weight, calculated to the total of the composition.

The second anionic surfactant is an alkyl sulfate or preferably ethoxylated alkyl ether sulfate surfactant or mixtures thereof with an alkyl chain length of $C_{10}$ to $C_{22}$.

Suitable surfactants are laureth sulfates, coceth sulfate, pareth sulfate, capryleth sulphate, myreth sulfate, oleth sulfate, deceth sulfate, trideceth sulfate, coco sulphate, $C_{10}$-$C_{16}$ alkyl sulphate, $C_{11}$-$C_{15}$ alkyl sulphate, $C_{12}$-$C_{18}$ alkyl sulphate, $C_{12}$-$C_{15}$ alkyl sulphate, $C_{12}$-$C_{16}$ alkyl sulphate, $C_{12}$-$C_{13}$ alkyl sulfate, lauryl sulphate, myrystyl sulphate, palm kernel sulphate, cetearyl sulfate, cetyl sulphate, decyl sulphate, oleyl sulphate, behenyl sulphate and/or their salts. All of the aforementioned anionic surfactants may or may not be ethoxylated at various degrees.

Cations for the surfactants may be selected from sodium, potassium, magnesium and/or ammonium.

The preferred second anionic surfactant is sodium laureth sulfate with 1-5 ethylene oxide units.

The composition comprises second anionic surfactant at a total concentration in the range of 5% to 12.5% by weight, calculated to the total of the composition.

The amphoteric surfactant is selected from compounds according to the general structure(s) II and/or III

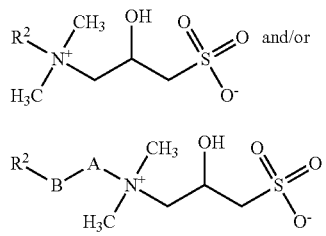

Formula II and/or

Formula III wherein $R^2$ is a straight or branched, saturated or unsaturated, substituted or unsubstituted alkyl chain with a carbon number of $C_{10}$ to $C_{22}$, preferably $R^2$ is a straight alkyl chain with a carbon number of $C_{10}$ to $C_{16}$, A is a straight alkyl chain with a carbon number of $C_1$ to $C_6$ or a branched alkyl chain with a carbon number of $C_3$ to $C_6$, preferably A is a linear alkyl chain with a carbon number of $C_3$, and B is an amide or an ester group.

Suitable compounds are known as hydroxysultain surfactants, such as cocoamidopropyl hydroxysultaine, laurylamidopropyl hydroxysultaine, erucamidopropyl hydroxysultaine, lauryl hydroxysultaine, and cocoyl hydrodroxysultaine.

The preferred amphoteric surfactant is lauryl hydroxysultaine.

The composition of the present invention comprises amphoteric surfactants at a concentration in the range of 0.1% to 2%, preferably 0.25% to 1.75%, more preferably 0.5% to 1.5% by weight, calculated to the total of the composition.

The weight ratio of total anionic surfactant to total amphoteric surfactant in the composition is in the range from 2.55 to 160, preferably from 7.75 to 64, and more preferably from 9 to 32, and wherein the weight ratio of the first anionic surfactant to the second anionic surfactant is in the range of 0.008 to 0.7, preferably 0.02 to 0.7, and more preferably from 0.1 to 0.7.

The weight ratio of second anionic surfactant to amphoteric surfactant is in the range of 2.5 to 125, preferably from 3.0 to 100, more preferably from 3.5 to 50, further more preferably from 4 to 25.

The weight ratio of first anionic surfactant to amphoteric surfactant in the composition is in the range of 0.067 to 30, preferably from 0.13 to 12, more preferably from 0.13 to 3.

In a particular embodiment, the composition comprises as the first anionic surfactant sodium lauroyl sarcosinate, as a second anionic surfactant sodium laureth sulfate with 1-5 ethoxylate units, and as amphoteric surfactant a lauryl hydroxysultaine, and the total concentration of the surfactants a) to c) is in the range from 6% to 18% by weight, preferably from 7% to 18% by weight, more preferably from 8% to 18% by weight, calculated to the total of the composition.

The composition comprises a compound according to the general structure

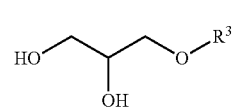

Formula IV wherein $R^3$ is a linear or branched alkyl chain with a total carbon number of $C_3$ to $C_{12}$, preferably $C_3$ to $C_8$, more preferably $R^3$ is a branched alkyl chain with a total carbon number of $C_8$.

Suitable compounds are propyl glycerine, butyl glycerine, pentyl glycerine, hexyl glycerine, heptyl glycerine, octyl glycerine, nonyl glycerine, decyl glycerine, undecyl glycerine, dodecyl glycrin, ethylhexyl glycerine.

The preferred compound is ethylhexyl glycerine.

The composition comprises the compound according to d) at a concentration in the range of 0.1% to 1% by weight, preferably from 0.2% to 1% by weight, more preferably from 0.25% to 1% by weight, calculated to the total of the composition.

The weight ratio of total surfactant to amphoteric surfactant is in the range of 1 to 20, preferably 2 to 18, more preferably 3 to 15.

In a particular embodiment, the composition of the present invention comprises one or more cationic polysaccharide(s) with a charge density below 1.5 meq/g, and/or aminated silicone(s) wherein the aminated silicone is in the form of a microemulsion.

Suitable cationic polysaccharides with a charge density below 1.5 meq/g are cationic cellulose and/or cationic guar derivatives. Cationic cellulose is known under its CTFA name Polyquaternium 10, whereas cationic guar derivatives are known as guar hydroxypropyltrimonium chloride or hydroxypropyl guar hydroxypropyltrimonium.

The preferred cationic polymer with a charge density below 1.5 meq/g is Polyquaternium 10.

The composition may further comprise aminated silicones in the form of a microemulsion. The term microemulsion within the meaning of the present invention is to be understood as an emulsion with a droplet size in the range of 50 nm to 1000 nm.

Suitable aminosilicone microemulsions are offered by Wacker Corp. under the trade names Wacker Belsil, in particular Wacker Belsil ADM 6057 and Wacker Belsil ADM 8020 VP. Further microemulsions are offered by Shin-Etsu Corp. under the trade name X-52-2265.

The preferred microemulsion is X-52-2265 from Shin-Etsu Corp.

The composition comprises each of the components, namely cationic polysaccharides and aminated silicones in the form of a microemulsion, at a concentration in the range of 0.1% to 3% by weight each, preferably 0.15% to 2% by weight each, more preferably 0.15% to 1.5% by weight each, calculated to the total of the composition.

The composition comprises cationic polysaccharides and aminated silicone microemulsion at a weight ratio in the range from 0.8 to 1.2.

The composition may comprise one or more foaming non-ionic surfactant(s) which is/are different from the compound(s) according to a) to d), at a concentration from 0.01% to 2% by weight, preferably from 0.1% to 1.5% by weight, more preferably from 0.25% to 1% by weight, calculated to the total of the composition.

Suitable non-ionic surfactants are in general all commonly known non-ionic surfactants available on the market.

Suitable examples for non-ionic surfactants are fatty alcohol ethoxylates of the following general structure $$R^4(OCH_2CH_2)_nOH$$

wherein $R^4$ is straight or branched, saturated or unsaturated alkyl chain which may be synthetic or natural with a C chain length in the range of 8 to 40, preferably 9 to 30 and more preferably 9 to 24 and n is a number in the range of 5 to 40, preferably 9 to 30.

Non-limiting suitable examples of the fatty alcohol ethoxylates are C9-11 Pareth-6, C9-11 Pareth-8, C9-15 Pareth-8, C11-13 Pareth-9, C11-13 Pareth-10, C11-15 Pareth-5, C11-15 Pareth-7, C11-15 Pareth-9, C11-15 Pareth-12, C11-15 Pareth-15, C11-15 Pareth-20, C11-15 Pareth-30, C11-15 Pareth-40, C11-21 Pareth-10, C12-13 Pareth-5, C12-13 Pareth-6, C12-13 Pareth-7, C12-13 Pareth-9, C12-13 Pareth-10, C12-13 Pareth-15, C12-13 Pareth-23, C12-14 Pareth-5, C12-14 Pareth-7, C12-14 Pareth-9, C12-14 Pareth-11, C12-14 Pareth-12, C12-15 Pareth-5, C12-15 Pareth-7, C12-15 Pareth-9, C12-15 Pareth-10, C12-15 Pareth-11, C12-15 Pareth-12, C12-16 Pareth-5, C12-16 Pareth-7, C12-16 Pareth-9, C13-15 Pareth-21, C14-15 Pareth-7, C14-15 Pareth-8, C14-15 Pareth-11, C14-15 Pareth-12, C14-15 Pareth-13, C20-22 Pareth-30, C20-40 Pareth-10, C20-40 Pareth-24, C20-40 Pareth-40, C20-40 Pareth-95, C22-24 Pareth-33, Beheneth-5, Beheneth-10, Beheneth-15, Beheneth-20, Beheneth-25, Beheneth-30, Ceteareth-5, Ceteareth-6, Ceteareth-7, Ceteareth-10, Ceteareth-11, Ceteareth-12, Ceteareth-15, Ceteareth-20, Ceteareth-25, Ceteareth-30, Ceteareth-35, Ceteareth-40, Laureth-5, Laureth-10, Laureth-15, Laureth-20, Laureth-25, Laureth-30, Laureth-40, Myreth-5, Myreth-10, Ceteth-5, Ceteth-10, Ceteth-15, Ceteth-20, Ceteth-25, Ceteth-30, Ceteth-40, Oleth-5, Oleth-10, Oleth-15, Oleth-20, Oleth-25, Oleth-30, Oleth-40, Steareth-5, Steareth-10, Steareth-15, Steareth-20, Steareth-25, Steareth-30, Steareth-35, and Steareth-40. They may also be comprised in the compositions as a mixture of more than one surfactant.

Further suitable nonionic surfactants are polypropylene glycol ethers of fatty alcohol according to general structure $$R^5(OCH_2(CH_3)CH_2)_nOH$$

wherein $R^5$ is straight or branched, saturated or unsaturated fatty alcohol which may be synthetic or natural with a C chain length in the range of 8 to 40, preferably 9 to 30 and more preferably 9 to 24 and n is a number in the range of 1 to 40, preferably 3 to 30.

Suitable non-limiting examples are PPG-3 Caprylyl ether, PPG-5 Caprylyl ether, PPG-10 Caprylyl ether, PPG-10 Cetyl ether, PPG-20 Cetyl ether, PPG-28 Cetyl ether, PPG-30 Cetyl ether, PPG-7 Lauryl ether, PPG-10 Lauryl ether, PPG-10 Oleyl ether, PPG-20 Oleyl ether, PPG-23 Oleyl ether, PPG-30 Oleyl ether, PPG-11 Stearyl ether and PPG-15 Stearyl ether.

Further suitable nonionic surfactants are polyethylene glycol fatty acid esters of the following general structure $$R^6C(O)(OCH_2CH_2)_nOH$$

wherein $R^6$ is straight or branched, saturated or unsaturated alkyl group which may be synthetic or natural with a C chain length in the range of 7 to 39, preferably 9 to 29 and more preferably 9 to 23 and n is a number in the range of 5 to 40, preferably 9 to 30.

Suitable non-limiting examples are PEG-8 Behenate, PEG-8 Caprate, PEG-8 Caprylate, PEG-5 Cocoate, PEG-8 Cocoate, PEG-9 Cocoate, PEG-10 Cocoate, PEG-15 Cocoate, PEG-6 Isopalmitate, PEG-6 Isostearate, PEG-8 Isostearate, PEG-9 Isostearate, PEG-10 Isostearate, PEG-12 Isostearate, PEG-20 Isostearate, PEG-30 Isostearate, PEG-40 Isostearate, PEG-6 Laurate, PEG-8 Laurate, PEG-9 Laurate, PEG-10 Laurate, PEG-12 Laurate, PEG-14 Laurate, PEG-20 Laurate, PEG-30 Laurate, PEG-8 Myristate, PEG-20 Myristate, PEG-5 Oleate, PEG-6 Oleate, PEG-7 Oleate, PEG-8 Oleate, PEG-9 Oleate, PEG-10 Oleate, PEG-11 Oleate, PEG-12 Oleate, PEG-15 Oleate, PEG-20 Oleate, PEG-30 Oleate, PEG-32 Oleate, PEG-6 Palmitate, PEG-18 Palmitate, PEG-20 Palmitate, PEG-5 Stearate, PEG-6 Stearate, PEG-7 Stearate, PEG-8 Stearate, PEG-9 Stearate, PEG-10 Stearate, PEG-12 Stearate, PEG-14 Stearate, PEG-15 Stearate, PEG-20 Stearate, PEG-25 Stearate, PEG-30 Stearate, PEG-35 Stearate and PEG-40 Stearate.

Further suitable nonionic surfactants are polypropylene glycol fatty acid esters of the following general structure $$R^7C(O)(OCH_2(CH_3)CH_2)_nOH$$

wherein $R^7$ is straight or branched, saturated or unsaturated alkyl group which may be synthetic or natural with a C chain length in the range of 7 to 39, preferably 9 to 29 and more preferably 9 to 23 and n is a number in the range of 1 to 40, preferably 9 to 30.

Suitable non-limiting examples are PPG-15 Isostearate, PPG-9 Laurate, PPG-26 Oleate and PPG-36 Oleate.

Further nonionic suitable surfactants are polyethylene glycol and polypropylene glycol ether of fatty alcohols of the following general structure $$R^8(OCH_2(CH_3)CH_2)_{n1}(OCH_2CH_2)_{n2}OH$$

wherein $R^8$ is straight or branched, saturated or unsaturated alkyl group which may be synthetic or natural with a C chain length in the range of 7 to 39, preferably 9 to 29 and more preferably 9 to 23 and n1 and n2 may be the same or different and are a number in the range of 1 to 40.

Suitable non-limiting examples are PPG-2 Ceteareth-9, PPG-4 Ceteareth-12, PPG-4 Ceteareth-20, PPG-2 C9-11 Pareth-5, PPG-2 C9-11 Pareth-7, PPG-2 C9-11 Pareth-8, PPG-2 C9-11 Pareth-11, PPG-2 C12-13 Pareth-8, PPG-2 C12-15 Pareth-6, PPG-4 C 13-15 Pareth-15, PPG-5 C9-15 Pareth-6, PPG-6 C9-11 Pareth-5, PPG-6 C12-15 Pareth-12, PPG-6 C12-18 Pareth-11, PPG-1 Deceth-4, PPG-1 Deceth-5, PPG-1 Deceth-6, PPG-1 Deceth-7, PPG-2 Deceth-3, PPG-2 Deceth-7, PPG-2 Deceth-8, PPG-2 Deceth-10, PPG-2 Deceth-15, PPG-2 Deceth-20, PPG-2 Deceth-30, PPG-2 Deceth-40, PPG-4 Deceth-4, PPG-4 Deceth-6, PPG-4 Deceth-6, PPG-6 Deceth-4, PPG-6 Deceth-9, PPG-8 Deceth-6, PPG-14 Deceth-6, PPG-2 Laureth-5, PPG-2 Laureth-8, PPG-2 Laureth-12, PPG-3 Laureth-8, PPG-3 Laureth-9, PPG-3 Laureth-10, PPG-3 Laureth-12, PPG-4 Laureth-2, PPG-4 Laureth-5, PPG-4 Laureth-7, PPG-4 Laurreth-15, PPG-5 Laureth-5, PPG-5 Laureth-3, PPG-Laureth-12, PPG-25 Laureth-25, PPG-3 Myreth-3, PPG-3 Myreth-11, PPG-9 Steareth-3, PPG-23 Steareth-34, PPG-30 Steareth-4, PPG-34 Steareth-3, and PPG-38 Steareth-6.

Further suitable nonionic surfactants are ethoxylated triglycerides. Well known and commonly used examples are ethoxylated castor oil such as PEG-40 hydrogenated castor oil or and PEG-60 hydrogenated castor oil.

Further suitable nonionic surfactants are alkyl polyglycosides with the general structure:

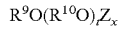

$$R^9O(R^{10}O)_tZ_x$$

Wherein Z denotes a reducing carbohydrate with $C_5$ to $C_6$, $R^9$ is an alkyl group with $C_8$ to $C_{18}$, $R^{10}$ is ehtyl or propyl, t ranges from 0 to 10, and x ranges from 1 to 5. Suitable compounds according to this structure are $C_9$-$C_{11}$ alkylpolyglycoside, the structures disclosed in EP-A 70 074, and JP 2015-123019A.

The composition may comprise one or more inorganic, monovalent salt(s) as a first thickening agent wherein the preferred salt is sodium chloride, and PEGylated or non-PEGylated esters of $C_{12}$ to $C_{18}$ fatty acids with pentaerythritol as a second thickening agent.

The viscosity of the composition of the present invention may be adjusted by thickening agents and should not exceed more than 30,000 mPas at 20° C. measured with Brookfield Rheometer at a shear rate of 5 sec$^{-1}$. Preferably the viscosity of the composition is in the range of 5,000 mPas to 25,000 mPas, more preferably 5,000 mPas to 20,000 mPas, each measured at 20° C. with Brookfield Rheometer at a shear rate of 5 sec$^{-1}$.

The composition comprises inorganic, monovalent salt(s) at a concentration in the range from 0.1% to 3.0% by weight, preferably from 0.2% to 2.5% by weight, more preferably from 0.5% to 2.0% by weight, calculated to the total of the composition.

The second thickening agent is PEGylated or non-PEGylated esters of $C_{12}$ to $C_{18}$ fatty acids with pentaerythritol. The preferred compound is PEG-150 pentaerythrityl tetrastearate.

Further suitable thickening agents may be nonionic thickening polymers. Suitable non-limiting examples are cellulose derivatives such as hydroxyethyl cellulose, methyl cellulose, hydroxymethyl cellulose, hydroxypropyl cellulose, guar gum and its derivatives, and konjac mannan and derivatives. Such Thickeners may be included at a concentration of 0.05 to 2.5% by weight calculated to total composition. Concentration of thickener is very much dependent on the thickener itself and also the preparation such as pH value of the composition etc. and therefore should be selected depending on the desired viscosity of the composition.

The composition of the present invention is transparent when being judged with the naked eye by an observer through a layer thickness of 1 cm. However, the composition may be colored with dyestuffs.

The composition according to the present invention may comprise dyestuffs wherein the dyestuffs are selected from non-ionic, nitro, cationic and/or anionic direct dyes.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87, HC Blue 17 and Basic Orange 31. The most preferred ones are Basic red 51, Basic Yellow 87 and Basic Orange 31 sold by BASF, HC Blue 17, Basic Blue 124.

Suitable neutral dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

The composition may comprise one or more hair direct dye at a total concentration of 0.001% to 10% by weight, preferably 0.005% to 7.5% by weight, and more preferably 0.01% to 5% by weight, calculated to the total of the composition. The composition can also comprise a mixture of several direct dyes, i.e., an anionic, a cationic and/or nonionic ones. In such a case the dyes may be mixed at any ratio with each other.

The pH of the compositions according to the present invention is suitably between 3.0 and 8.0 and preferably in the range of 3.5 to 6.5, more preferably 4.5 to 6.0 and most preferably 4.5 to 5.5.

In principle, the pH of the composition can be adjusted with any organic and/or inorganic acid(s) or base or their mixtures. Suitable acids are phosphoric acid, hydrochloric acid as the inorganic ones and to the organic acids the well-known citric acid and lactic acid, glycolic acid, glyoxylic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. Suitable bases are sodium hydroxide or potassium hydroxide.

The composition of the present invention may additionally comprise any compound customarily found in cleansing compositions such as chelating agents, preservatives and fragrance.

Suitable chelating agents are selected from polycarboxy acids. The preferred one is ethylene diamine tetraacetic acid, i.e. EDTA. A typical useful concentration range for chelating agents is 0.01% to 2.5% by weight, calculated to the total composition.

The composition of the present invention may comprise one or more organic solvents. Suitable organic solvents are ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, butylene glycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol.

The most preferred ones are butylene glycol, ethanol, isopropanol, benzylalcohol and polypropylene glycols.

The concentration of organic solvents should not exceed 10%, and preferably range from 0.1% to 7.5% by weight, more preferably from 0.1% to 5% by weight, calculated to the total of the composition.

The skilled in the art will recognize that the majority of the aforementioned organic solvents may act as preservatives as well. However, the composition of the present invention may comprise any other known preservative or preservative mixture besides and/or including organic solvents.

The composition of the present invention may further comprise one or more UV filters which may be selected from water soluble ones as well as oils soluble ones. The oil soluble UV filter are more preferred ones as they show no interaction with the cationic quaternary ammonium polymers. Non-limiting examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher, and/or polysilicone-15.

The total UV filter concentration may be in the range of 0.01% to 1% by weight, calculated to the total composition.

In a further embodiment of the present invention, the composition may comprise one or more ubiquinone derivatives of the following general structure

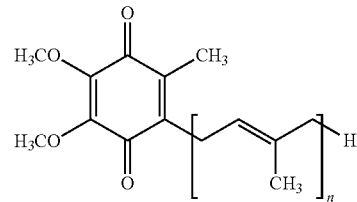

where n is a number between 1 and 10. It should be noted that the compositions of the present invention can certainly comprise more than one ubiquinone. Preferred ubiquinones are the ones where n is a number between 6 and 10 and especially preferred is Ubiquinone 50 where n is 10, also known as Coenzyme Q10.

The composition may further comprise one or more amino acid(s). Suitable amino acids may be all of the known amino acids such as arginine, alanine, asparagine, glutamine, glycine, histidine, leucine, lysine, methionine, phenylalanine, proline, serine, threonine, tryptophan, tyrosine and valine.

The concentration of amino acids may be in the range of 0.01% to 5% by weight, preferably 0.1% to 3% by weight, and more preferably 0.2% to 2.5% by weight, and most preferably 0.25% to 2% by weight, calculated to the total of the composition.

The composition of the present invention may further comprise any known vitamin and/or antioxidant.

The following examples are to illustrate the present invention, but not to limit it.

EXAMPLE 1

The following compositions were prepared:

TABLE 1

| | Compositions | |
|---|---|---|
| Ingredient | Comparative composition % [w/w] | Inventive composition % [w/w] |
| Sodium laureth sulfate | 15 | 12 |
| Sodium lauroyl sarcosinate | 5 | 3 |
| Lauryl Hydroxysultaine | 2 | 1.5 |
| Ethylhexylglycerin | — | 0.875 |
| Amodimethicone* | 0.3 | — |
| Amodimethicone microemulsion** | — | 0.3 |
| Water | Ad 100 | |
| Total amount of washing active substances | 22 | 14.875 |

*DC 2-8566 from Dow Corning Corp.
**X-52-2265 from Shin-Etsu Corp.

The pH of the compositions was adjusted with lactic acid to 5.5.

Foaming properties of the above compositions were measured with a Sita Foam Tester R-2000 instrument. Equal amounts of surfactant solutions were foamed for 10 s at 1000 rpm over 4 cycles. The resulting foam volume was recorded.

TABLE 2

Foaming properties of comparative and inventive compositions

| # of foaming cycles | Foam volume comparative composition [mL] | Foam volume inventive composition [mL] |
|---|---|---|
| 1 | 304 | 306 |
| 2 | 420 | 473 |
| 3 | 474 | 557 |
| 4 | 580 | 640 |

As a result of the foaming experiment, the inventive composition produced higher foam volumes compared to the comparative composition.

Color retention was investigated on oxidatively colored hair streaks supplied by International Hair Importers, Glendale, N.Y., USA. The surfactant compositions were diluted with water at a volume ratio 1:9 and heated to 40° C. in a shaking bath at a speed of 80 rpm. Each hair streak was immersed in the shaking bath for 60 s, then rinsed with water for 20 s; towel dried, and the process was repeated for another 19 times. Color values in the L*ab color space were recorded prior to the experiment and after 20 washing cycles. The difference in color is reported as ΔE.

As a result, the hair streaks washed with the comparative composition had a color difference over 20 washing cycles of ΔE=9.4±0.4, whereas the hair streaks treated with the inventive composition had a color difference of ΔE=8.1±0.5.

Thus, the inventive composition led to lower color fading and, therefore, showed higher washfastness.

The following examples are within the scope of the present invention and show a similar effect.

EXAMPLE 2

| Ingredients | % by weight |
|---|---|
| Sodium laureth sulfate | 8.0 |
| Sodium lauroyl sarcosinate | 2.0 |
| Lauryl hydroxysultaine | 2.0 |
| Ethylhexylglycerin | 0.5 |
| Polyquaternium 10 | 0.3 |
| Amodimethicone microemulsion* | 0.28 |
| Sodium chloride | 1.0 |
| PEG-150 Pentaerythrityl Tetrastearate | 0.15 |
| C12-C14 Pareth-12 | 0.1 |
| Propylene glycol | 0.1 |
| Preservatives | q.s. |
| Water | ad 100 |

*X-52-2265 from Shin-Etsu Corp.

EXAMPLE 3

| Ingredients | % by weight |
|---|---|
| Sodium laureth sulfate | 12.5 |
| Sodium lauroyl sarcosinate | 1.0 |
| Lauryl hydroxysultaine | 2.0 |
| Ethylhexylglycerin | 1.0 |
| Polyquaternium 10 | 0.5 |
| Amodimethicone microemulsion* | 0.6 |
| Sodium chloride | 2.0 |
| PEG-150 Pentaerythrityl Tetrastearate | 0.25 |
| Trideceth-10 | 0.5 |
| Butylene glycol | 0.25 |
| Preservatives | q.s. |
| Water | ad 100 |

*Wacker Belsil ADM 8020 VP

EXAMPLE 4

| Ingredients | % by weight |
|---|---|
| Sodium lauryl sulfate | 5.0 |
| Sodium myristoyl sarcosinate | 3.0 |
| Laurylamidopropyl hydroxysultaine | 2.0 |
| Ethylhexylglycerin | 1.5 |
| Polyquaternium 10 | 1.0 |
| Amodimethicone microemulsion* | 0.9 |
| Sodium chloride | 1.5 |
| PEG-150 Pentaerythrityl Tetrastearate | 0.5 |
| Trideceth-10 | 1.0 |
| Ethanol | 1.0 |
| Preservatives | q.s. |
| Water | ad 100 |

*Wacker Belsil ADM 8020 VP

EXAMPLE 5

| Ingredients | % by weight |
|---|---|
| Sodium laureth sulfate | 8.0 |
| Sodium lauroyl sarcosinate | 2.0 |
| Lauryl hydroxysultaine | 2.0 |
| Ethylhexylglycerin | 0.5 |
| Polyquaternium 10 | 0.3 |
| Amodimethicone microemulsion* | 0.28 |
| Sodium chloride | 1.0 |
| PEG-150 Pentaerythrityl Tetrastearate | 0.15 |
| C12-C14 Pareth-12 | 0.1 |
| Propylene glycol | 0.1 |
| HC Blue 6 | 0.1 |
| EDTA | 0.3 |
| $C_9$-$C_{11}$ alkylpolyglycoside | 0.5 |
| Preservatives | q.s. |
| Water | ad 100 |

*X-52-2265 from Shin-Etsu Corp.

The invention claimed is:

1. An aqueous cleansing composition for keratin fibers, comprising surfactants at a total concentration in a range of 8% to 19% by weight, calculated to the total of the aqueous composition, wherein the aqueous composition comprises the following surfactants
 a) a first anionic surfactant selected from cocoyl sarcosinate and its salts, lauroyl sarcosinate and its salts, myristoyl sarcosinate and its salts, stearoyl sarcosinate and its salts, oleoyl sarcosinate and its salts, and palmitoyl sarcosinate and its salts, wherein the salts are formable with cations selected from sodium, potassium, magnesium, and ammonium ions;
 b) a second anionic surfactant selected from laureth sulfate, coceth sulfate, pareth sulfate, capryleth sulphate, myreth sulfate, oleth sulfate, deceth sulfate, trideceth sulfate, coco sulphate, $C_{10}$-$C_{16}$ alkyl sulphate, $C_{11}$-$C_{15}$ alkyl sulphate, $C_{12}$-$C_{18}$ alkyl sulphate, $C_{12}$-$C_{15}$ alkyl sulphate, $C_{12}$-$C_{16}$ alkyl sulphate, $C_{12}$-$C_{13}$ alkyl sulfate, lauryl sulphate, myrystyl sulphate, palm kernel sulphate, cetearyl sulfate, cetyl sulphate, decyl sulphate, oleyl sulphate, behenyl sulphate, and their salts;
c) an amphoteric surfactant that is a hydroxysultain surfactant selected from cocoamidopropyl hydroxysultaine, laurylamidopropyl hydroxysultaine, erucamidopropyl hydroxysultaine, lauryl hydroxysultaine, and cocoyl hydrodroxysultaine;

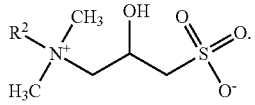

d) a compound selected from propyl glycerine, butyl glycerine, pentyl glycerine, hexyl glycerine, heptyl glycerine, octyl glycerine, nonyl glycerine, decyl glycerine, undecyl glycerine, dodecyl glycrin, ethylhexyl glycerine; and
e) at least one aminated silicone in the form of the microemulsion having droplet sizes in the range of 50 nm to 1000 nm,
wherein the aqueous composition is transparent when being judged with the naked eye by an observer through a layer thickness of 1 cm.

2. The aqueous composition of claim 1, wherein a total concentration of compound d) is 0.1% to 1% by weight, calculated to the total of the aqueous composition.

3. The aqueous composition of claim 1, further comprising one or more cationic polysaccharide(s) with a charge density below 1.5 meq/g.

4. The aqueous composition of claim 3, wherein a total weight ratio of cationic polysaccharides to the at least one aminated silicone is from 0.8 to 1.2.

5. The aqueous composition of claim 1, wherein a weight ratio of the total anionic surfactant to the total amphoteric surfactant is from 2.55 to 160, and a weight ratio of the first anionic surfactant to the second anionic surfactant is 0.008 to 0.7.

6. The aqueous composition of claim 1, wherein the surfactant a) is present at a total concentration of 0.1% to 3.5% by weight, calculated to the total of the aqueous composition.

7. The aqueous composition of claim 1, further comprising:
one or more inorganic, monovalent salt(s) as a first thickening agent, and PEGylated or non-PEGylated esters of $C_{12}$ to $C_{18}$ fatty acids with pentaerythritol as a second thickening agent.

8. The aqueous composition of claim 7, wherein a total inorganic, monovalent salt concentration is from 0.1% to 3.0% by weight, calculated to the total of the aqueous composition.

9. The aqueous composition of claim 1, further comprising:
one or more foaming non-ionic surfactant(s) that is/are different from surfactants a) to c) and compound d), at a total concentration from 0.01% to 2% by weight, calculated to the total of the aqueous composition.

10. The aqueous composition of claim 1, wherein the first anionic surfactant is sodium lauroyl sarcosinate, the second anionic surfactant is sodium laureth sulfate with 1-5 ethylene oxide units, the amphoteric surfactant is lauryl hydroxysultaine, and a total concentration of surfactants a) to c) is from 8% to 18% by weight, calculated to the total of the composition.

11. The aqueous composition of claim 1, further comprising:
dyestuffs selected from the group consisting of non-ionic, nitro, cationic, anionic direct dyes, and at least one combination thereof.

12. A kit-of-parts comprising the aqueous composition of claim 1 and at least one further item selected from at least one of a hair conditioning composition and a hair styling composition.

13. The aqueous composition of claim 1, wherein $R^1$ of the first anionic surfactant is a straight alkyl chain with a carbon number of $C_9$ to $C_{17}$.

14. The aqueous composition of claim 1, wherein the second anionic surfactant is an ethoxylated alkyl ether sulphate surfactant.

15. The aqueous composition of claim 1, where in $R^2$ of the amphoteric surfactant is a straight alkyl chain with a carbon number of $C_{10}$ to $C_{16}$.

16. The aqueous composition of claim 1, where A of the amphoteric surfactant is a linear alkyl chain with a carbon number of $C_3$.

17. The aqueous composition of claim 1, wherein $R^3$ of compound d) is a linear or branched alkyl chain with a carbon number of $C_3$ to $C_8$.

18. The aqueous composition of claim 1, wherein $R^3$ of compound d) is a linear or branched alkyl chain with a carbon number of $C_8$.

19. A method for cleansing or for reducing wash fastness of artificially colored keratin fibers, comprising:
applying the aqueous composition of claim 1 onto wet hair; and
massaging and rinsing the composition off the hair with water after a treatment time from 30 seconds to 600 seconds.

* * * * *